(12) United States Patent
Aghassian (10) Patent No.: US 9,713,717 B2
(45) Date of Patent: Jul. 25, 2017

(54) IMPLANTABLE STIMULATOR DEVICE HAVING COMPONENTS EMBEDDED IN A CIRCUIT BOARD

(71) Applicant: Boston Scientific Neuromodulation Corporation, Valencia, CA (US)

(72) Inventor: Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 15 days.

(21) Appl. No.: 14/537,687

(22) Filed: Nov. 10, 2014

(65) Prior Publication Data

US 2015/0157861 A1    Jun. 11, 2015

Related U.S. Application Data

(60) Provisional application No. 61/913,828, filed on Dec. 9, 2013.

(51) Int. Cl.
*A61N 1/36* (2006.01)
*A61N 1/375* (2006.01)
*A61N 1/05* (2006.01)

(52) U.S. Cl.
CPC ....... *A61N 1/36125* (2013.01); *A61N 1/0551* (2013.01); *A61N 1/3605* (2013.01); *A61N 1/3758* (2013.01); *A61N 1/36142* (2013.01)

(58) Field of Classification Search
CPC .... A61N 1/05; A61N 1/0551; A61N 1/36125; A61N 1/36142; A61N 1/3758
USPC .......................................................... 607/2
See application file for complete search history.

(56) References Cited

U.S. PATENT DOCUMENTS

| | | | |
|---|---|---|---|
| 3,517,663 A * | 6/1970 | Bowers ................. | A61N 1/371 324/103 R |
| 5,963,429 A | 10/1999 | Chen | |
| 6,181,969 B1 | 1/2001 | Gord | |
| 6,411,854 B1 | 6/2002 | Tziviskos et al. | |
| 6,516,227 B1 | 2/2003 | Meadows et al. | |
| 7,856,260 B1 | 12/2010 | Ryu | |
| 7,881,803 B2 | 2/2011 | Parramon et al. | |

(Continued)

OTHER PUBLICATIONS

U.S. Appl. No. 14/470,854, Funderburk, filed Aug. 27, 2014.

(Continued)

*Primary Examiner* — Christopher A Flory
(74) *Attorney, Agent, or Firm* — Lewis, Reese & Nesmith, PLLC (57) ABSTRACT

An improved circuit board for an implantable stimulator device is disclosed having components embedded within the device's circuit board, and in particular having embedded components in the electrodes current paths, such as various numbers and/or combinations of DC-blocking capacitors, EMI filtering capacitors, and EMI filtering inductors. By embedding at least some of these components, the improved circuit board can accommodate additional IPG circuitry, or can be made smaller, which is significant given the trend to increase the number of electrodes in such devices. In a preferred embodiment, at least the filtering capacitors are embedded in the circuit board, while the DC-blocking capacitors are traditionally surface mounted, without reducing the number of DC-blocking capacitors compared to the number of electrodes the IPG supports.

23 Claims, 11 Drawing Sheets

(56) References Cited

U.S. PATENT DOCUMENTS

| | | | |
|---|---|---|---|
| 2001/0051766 A1* | 12/2001 | Gazdzinski | A61B 1/00016 600/309 |
| 2002/0166618 A1* | 11/2002 | Wolf | A61N 1/3754 156/89.12 |
| 2005/0007718 A1* | 1/2005 | Stevenson | A61N 1/3754 361/118 |
| 2005/0245970 A1 | 11/2005 | Erickson et al. | |
| 2005/0248907 A1* | 11/2005 | Stevenson | A61N 1/3754 361/306.2 |
| 2007/0038250 A1 | 2/2007 | He et al. | |
| 2007/0080387 A1* | 4/2007 | Liu | H01L 28/82 257/303 |
| 2007/0096823 A1* | 5/2007 | Wang | H03F 1/30 330/285 |
| 2007/0097658 A1* | 5/2007 | Yang | H05K 1/0231 361/780 |
| 2007/0100399 A1* | 5/2007 | Parramon | A61N 1/36125 607/68 |
| 2008/0020488 A1* | 1/2008 | Clevenger | H01L 21/76898 438/3 |
| 2008/0097543 A1* | 4/2008 | Zhu | A61N 1/3712 607/28 |
| 2008/0114405 A1* | 5/2008 | Palmer | A61N 1/37 607/2 |
| 2008/0192967 A1 | 8/2008 | Chan et al. | |
| 2008/0247117 A1* | 10/2008 | Elam | A61N 1/3754 361/302 |
| 2009/0184090 A1 | 7/2009 | Wuchse et al. | |
| 2009/0187228 A1* | 7/2009 | Zhang | A61N 1/3712 607/28 |
| 2009/0222066 A1 | 9/2009 | Chen et al. | |
| 2010/0034410 A1* | 2/2010 | Link | H04R 25/60 381/328 |
| 2010/0100164 A1* | 4/2010 | Johnson | H01F 27/027 607/116 |
| 2010/0149042 A1* | 6/2010 | Utsi | H01Q 1/273 343/700 MS |
| 2010/0151113 A1* | 6/2010 | Shelton | A61B 5/0031 427/2.24 |
| 2010/0156537 A1* | 6/2010 | Dishop | H03F 3/211 330/276 |
| 2010/0231327 A1* | 9/2010 | Johnson | H01F 27/027 333/175 |
| 2010/0268309 A1* | 10/2010 | Parramon | A61N 1/36185 607/116 |
| 2011/0004283 A1* | 1/2011 | Stevenson | H01G 4/40 607/116 |
| 2011/0098776 A1* | 4/2011 | Zhu | A61N 1/3712 607/28 |
| 2011/0216513 A1* | 9/2011 | Lee | H05K 1/185 361/761 |
| 2011/0309884 A1* | 12/2011 | Dishop | H03F 3/211 330/276 |
| 2012/0092031 A1* | 4/2012 | Shi | A61N 1/025 324/691 |
| 2012/0095519 A1* | 4/2012 | Parramon | A61N 1/37241 607/2 |
| 2012/0095529 A1* | 4/2012 | Parramon | A61N 1/372 607/59 |
| 2012/0228014 A1* | 9/2012 | Das | H05K 1/162 174/260 |
| 2012/0248981 A1* | 10/2012 | Karalis | H03H 7/40 315/70 |
| 2012/0253420 A1* | 10/2012 | Zhu | A61N 1/3712 607/28 |
| 2013/0002496 A1* | 1/2013 | Utsi | H01Q 1/273 343/718 |
| 2013/0090706 A1* | 4/2013 | Nudo | A61N 1/36103 607/62 |
| 2013/0122658 A1* | 5/2013 | Savic | H01L 23/24 438/126 |
| 2013/0176692 A1* | 7/2013 | Haslebner | H05K 3/4688 361/748 |
| 2013/0184796 A1* | 7/2013 | Marzano | A61N 1/3754 607/116 |
| 2013/0184797 A1* | 7/2013 | Tang | A61N 1/3754 607/116 |
| 2013/0233603 A1* | 9/2013 | Weichslberger | H05K 1/142 174/257 |
| 2013/0235550 A1* | 9/2013 | Stevenson | H01G 4/40 361/818 |
| 2013/0282079 A1* | 10/2013 | Kallmyer | A61N 1/36125 607/62 |
| 2013/0289665 A1 | 10/2013 | Marnfeldt et al. | |
| 2014/0036409 A1* | 2/2014 | Stevenson | A61N 1/3754 361/302 |
| 2014/0155970 A1 | 6/2014 | Bocek et al. | |
| 2014/0277234 A1* | 9/2014 | O'Flynn | A61N 1/0587 607/17 |
| 2015/0066124 A1* | 3/2015 | Stevenson | H01G 4/40 607/119 |
| 2015/0086051 A1* | 3/2015 | Link | H04R 25/60 381/312 |
| 2015/0097734 A1* | 4/2015 | Zhao | A61B 5/0022 343/702 |
| 2015/0134039 A1* | 5/2015 | Marzano | A61N 1/3754 607/116 |
| 2015/0297892 A1* | 10/2015 | Tol | A61N 1/36125 600/378 |
| 2015/0342053 A1* | 11/2015 | Savic | H01L 23/24 361/761 |

OTHER PUBLICATIONS

A. Seki, "PCBs With Embedded Components Emerge for Capacitors," Asia Electronics Industry (AEI), p. 24 (Mar. 2011).

International Search Report and Written Opinion regarding corresponding PCT Application No. PCT/US2014/065036, dated Jun. 30, 2015.

* cited by examiner

IMPLANTABLE STIMULATOR DEVICE HAVING COMPONENTS EMBEDDED IN A CIRCUIT BOARD

CROSS REFERENCE TO RELATED APPLICATIONS

This is a non-provisional of U.S. Provisional Patent Application Ser. No. 61/913,828, filed Dec. 9, 2013, which is incorporated herein by reference, and to which priority is claimed.

FIELD OF THE INVENTION

The present invention relates to implantable stimulator devices, and in particular to minimizing the size of the circuitry in the implantable stimulator by embedding certain components within a circuit board in the device.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable medical device or in any implantable medical device system.

Figure 1A:
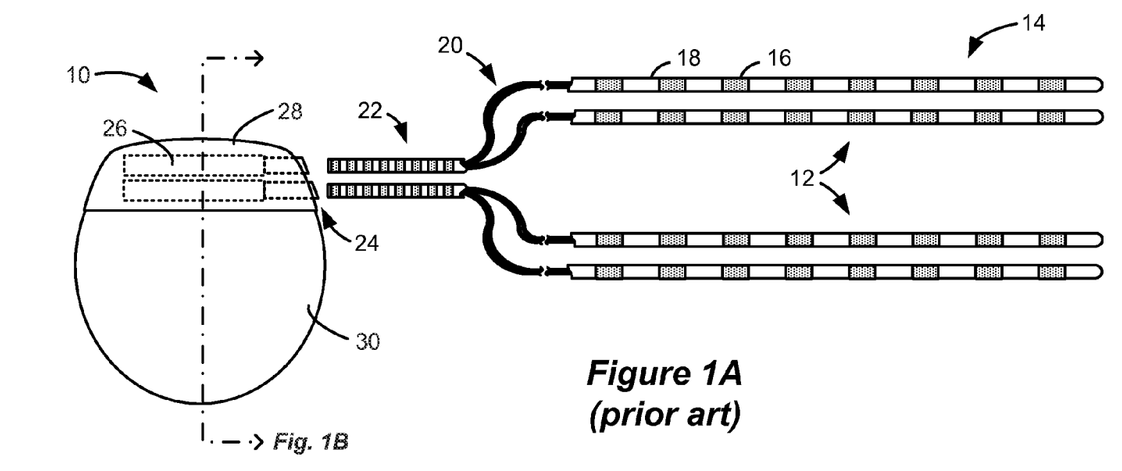
FIGS. 1A and 1B show different views of an implantable medical device, specifically an Implantable Pulse Generator (IPG) having a number of electrodes, in accordance with the prior art.
Figure 1B:
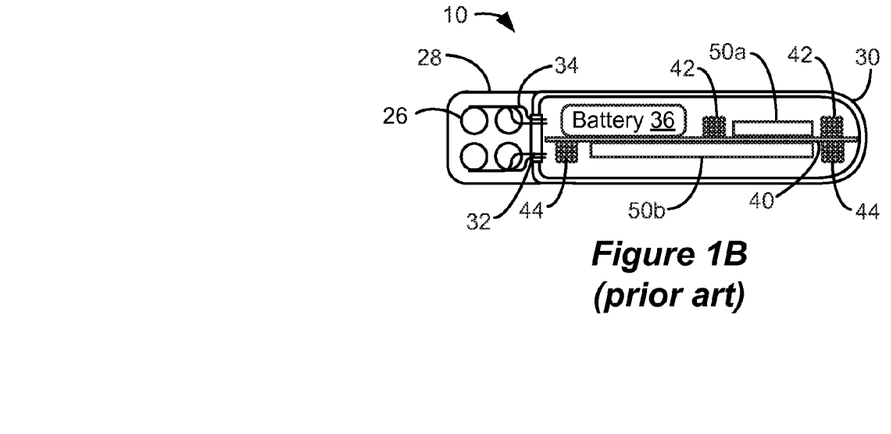

An SCS system typically includes an Implantable Pulse Generator (IPG) 10 shown in plan and cross-sectional views in FIGS. 1A and 1B. The IPG 10 includes a biocompatible device case 30 that holds the circuitry and battery 36 necessary for the IPG to function. The IPG 10 is coupled to electrodes 16 via one or more electrode leads 14 that form an electrode array 12. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 28 on the IPG 10, which header can comprise an epoxy for example. Once inserted, the proximal contacts 22 connect to header contacts 26, which are in turn coupled by feedthrough pins 34 through a case feedthrough 32 to circuitry within the case 30.

In the illustrated IPG 10, there are thirty-two lead electrodes (E1-E32) split between four leads 14, with the header 28 containing a 2×2 array of lead connectors 24. However, the number of leads and electrodes in an IPG is application specific and therefore can vary. In a SCS application, the electrode leads 14 are typically implanted proximate to the dura in a patient's spinal cord, and when a four-lead IPG 10 is used, these leads are usually split with two on each of the right and left sides of the dura. The proximal electrodes 22 are tunneled through the patient's tissue to a distant location such as the buttocks where the IPG case 30 is implanted, at which point they are coupled to the lead connectors 24. A four-lead IPG 10 can also be used for Deep Brain Stimulation (DBS) in another example. In other IPG examples designed for implantation directly at a site requiring stimulation, the IPG can be lead-less, having electrodes 16 instead appearing on the body of the IPG for contacting the patient's tissue.

As shown in the cross section of FIG. 1B, the IPG 10 includes a printed circuit board (PCB) 40. Electrically coupled to the PCB 40 are the battery 36, which in this example is rechargeable; other circuitry 50a and 50b coupled to top and bottom surfaces of the PCB; a communication coil 42 for wirelessly communicating with an external controller (not shown); a charging coil 44 for wirelessly receiving a magnetic charging field from an external charger (not shown) for recharging the battery 36; and the feedthrough pins 34 (connection not shown). If battery 36 is permanent and not rechargeable, charging coil 44 would be unnecessary. (Further details concerning operation of the coils 42 and 44 and the external devices with which they communicate can be found in U.S. patent application Ser. No. 14/470,854, filed Aug. 27, 2014).

Figure 2A:
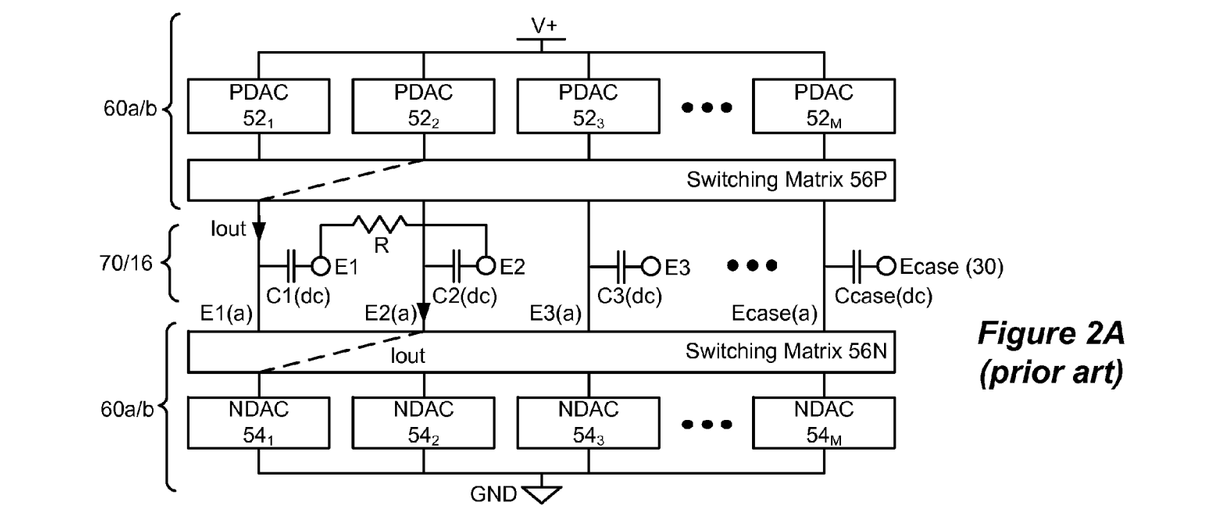
FIGS. 2A and 2B show current distribution circuitry for an IPG, including the use of DC-blocking capacitors in electrode current paths, in accordance with the prior art.
Figure 2B:
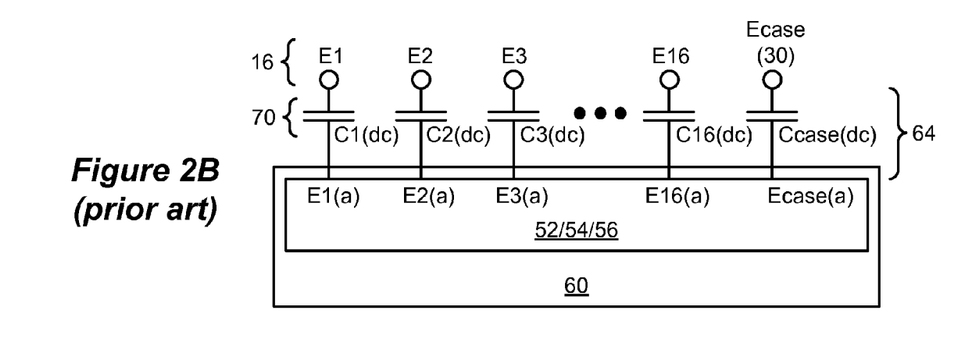

FIGS. 2A and 2B show some of the other circuitry 50a or 50b present in the IPG 10, and in particular FIG. 2A shows current distribution circuitry used to establish a current at any of the lead electrodes 16, which currents may comprise uni-phasic or multi-phasic current pulses. In this example, the current distribution circuitry includes a number of current sources (PDACs 52) and current sinks (NDACs 54). The PDACs 52 and NDACs 54 comprise Digital-to-Analog converters (DACs) able to respectively source and sink a current pulse of a desired amplitude Iout, which amplitude may be controllable in accordance with digital control signals (not shown). ("PDAC" and "NDAC" are so called because they are typically made from P-channel and N-channel transistors respectively). The sourced or sunk current from one or more active PDACs 52 or NDACs 54 is directed to selected electrodes 16 via switch matrices 56P and 56N, which are also digitally controlled (not shown). Note that the current distribution circuitry in this example also supports selection of the conductive case 30 as an electrode (Ecase 30), which case electrode 30 is typically selected for monopolar stimulation, as is well known. DACs 52 and 54 can also comprise voltage sources. The sourcing components (PDACs 52, matrix 56P) and the sinking components (NDACs 54, matrix 56N) can individually also be considered as current distribution circuitry.

Proper control of the DACs 52 and 54 and the switching matrices 56 allows any of the electrodes 16 to act as anodes or cathodes to create a current through a patient's tissue, R, hopefully with good therapeutic effect. In the example shown, PDAC $52_2$ is controlled to source a current of amplitude Iout to anode electrode E1 via switch matrix 56P, while NDAC $54_1$ is controlled to sink a current of amplitude Iout from cathode electrode E2 via switching matrix 56N. The DACs 52 and 54 can also be programmed to issue the current pulses with a particular frequency and duration, although this detail is unimportant to the present disclosure. Power for the current distribution circuitry is provided by a power supply voltage V+, as described in further detail in U.S. Patent Application Publication 2013/0289665 for example. More than one anode electrode and more than one cathode electrode may be selected at one time, and thus current can flow between two or more of the electrodes 16.

Other current distribution circuitries can also be used in IPG 10. For example, in an example not using switching matrices 56, each electrode Ei can be provided with a dedicated PDAC $52i$ and NDAC $54i$, such as is disclosed in U.S. Pat. No. 6,181,969 for example. In another example, the PDACs 52 and NDACs 54 may provide currents of fixed amplitudes, with multiple of these DACs being selected by the switching matrices 56 to provide a sum of their currents at a selected electrode, such as described in U.S. Patent Application Publications 2007/0038250 and 2007/0100399.

Much of the current distribution circuitry of FIG. 2A, including the DACs 52 and 54 and the switch matrices 56, can be integrated on an Application Specific Integrated Circuit (ASIC) 60, as shown in FIG. 2B. In the example shown, ASIC 60 contains circuitry to support sixteen lead electrodes 16 and the case electrode 30. In a 32-electrode IPG 10, two such ASIC 60*a* and 60*b* are used, with the case electrode 30 being activated in only one of the ASICs 60*a* or 60*b*, in effect creating a 33-electrode device. ASICs 60*a* and 60*b* can be identically fabricated, and controlled by a microcontroller integrated circuit 62 (FIG. 3) acting as their master, as disclosed in U.S. Patent Application Publications 2012/0095529, 2012/0092031, and 2012/0095519. ASICs 60*a* and 60*b* may also contain other circuitry useful in the IPG 10, such as battery charging and protection circuitry (for interfacing off chip with the battery 36 and charging coil 44), telemetry circuitry (for interfacing off chip with telemetry coil 42), various measurement circuits, etc.

Also shown in FIGS. 2A and 2B are DC-blocking capacitors 70 (C(dc)) coupled to each of the electrode current paths 64 between the electrodes nodes Ei(a) present at the ASICs 60*a/b* (i.e., the outputs of the current distribution circuitry) and the electrodes 16 (Ei). The DC-blocking capacitors 70 are placed in series in the electrode current paths 64, and act as a safety measure to prevent DC current injection into the patient, and are commonly used in IPGs.

Given the amplitudes of the currents (Iout) typically provided to the electrodes 16 for effective therapy (on the order of milliAmps), and given the desire to prevent large voltages from building up across the DC-blocking capacitors 70 when passing such currents, the DC-blocking capacitors 70 have relatively large capacitance values—typically on the order of 1-10 microFarads. The DC-blocking capacitors 70 are thus relatively large in physical size, and can take up considerable space within the case 30 of the IPG 10, and in particular on the IPG's PCB 40.

Figure 3:
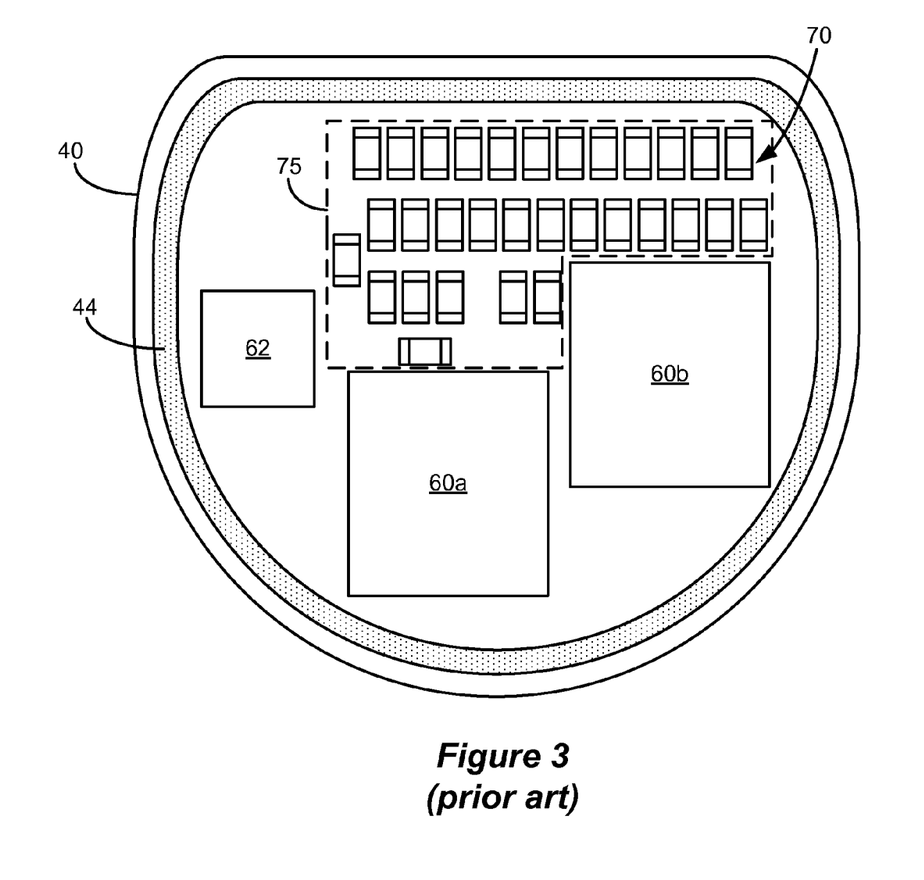
FIG. 3 shows a printed circuit board (PCB) for an IPG including the DC-blocking capacitors, in accordance with the prior art.

This is shown in FIG. 3 for the 32-electrode IPG 10 described earlier, which shows the bottom surface of PCB 40 to which the charging coil 44 is mounted. Also mounted to the PCB 40 within the charging coil 44 are the ASICs 60*a* and 60*b* (each supporting 16 electrodes, and one supporting the case electrode 30), the master microcontroller 62, and the DC-blocking capacitors 70. As one skilled in the art will appreciate, the PCB 40 would contain other components as well, but these are not shown for simplicity. The DC-blocking capacitors 70 comprise typical surface-mountable ceramic capacitors, each of which may have a footprint or area of 120×60 mils (what is known in the art as a "1206" capacitor), 80×50 mils (an "0805" capacitor), or smaller.

Taken together, the DC-blocking capacitors 70 take up a relatively large area 75 on the bottom surface of the PCB 40, which may be as high as 30% of the total area of that surface (typically on the order of 10 cm$^2$). This is unfortunate, because the DC-blocking capacitors 70 increase the size of the PCB 40, which increases the size of the case 30 and the IPG 10, which is preferably kept as small as possible to ease implantation surgery and promote patient comfort. The problem of the size of the DC-blocking capacitors 70 is further exacerbated by the industry's desire to provide IPGs with greater number of electrodes to provide patients with finer resolution and more-complex stimulation therapies. While at least some of the DC-blocking capacitors 70 could theoretically be placed on the other (top) surface of the PCB 40, this is not always an option: for example, in the example of IPG 10, the top surface of the PCB 40 is already fully occupied by the communication coil 42, the battery 36, and other surface-mounted circuitry 50*a*, as shown in FIG. 1B.

The prior art has recognized the problem of relatively-large DC-blocking capacitors 70 in a multi-electrode IPG. However, known solutions to this problem seek to minimize the number of DC-blocking capacitors 70 used. For example, in U.S. Pat. No. 7,881,803, an IPG is provided having only a single DC-blocking capacitor, which saves room in the IPG and hence allows for IPG miniaturization. U.S. Patent Application Publication 2010/0268309 likewise proposes an IPG with a reduced number of DC-blocking capacitors, i.e., less than the number of electrodes the IPG supports.

However, merely reducing the number of DC-blocking capacitors 70 as suggested by the art is not viewed by the inventor as a sufficient manner for addressing this problem. If too many DC-blocking capacitors 70 are removed compared to the number of electrodes the IPG supports, difficulties can arise. Therapy can be compromised, as the ability to freely choose electrodes operable as the anodes or cathodes may be restrained, because certain selectable current paths may not include a DC-blocking capacitor 70 as desired for safety; additional design complexities of the current distribution circuitry must be undertaken to address this concern. By contrast, if too few DC-blocking capacitors 70 are removed compared to the number of IPG electrodes 16, space savings in the IPG may be insignificant.

Figure 4A:
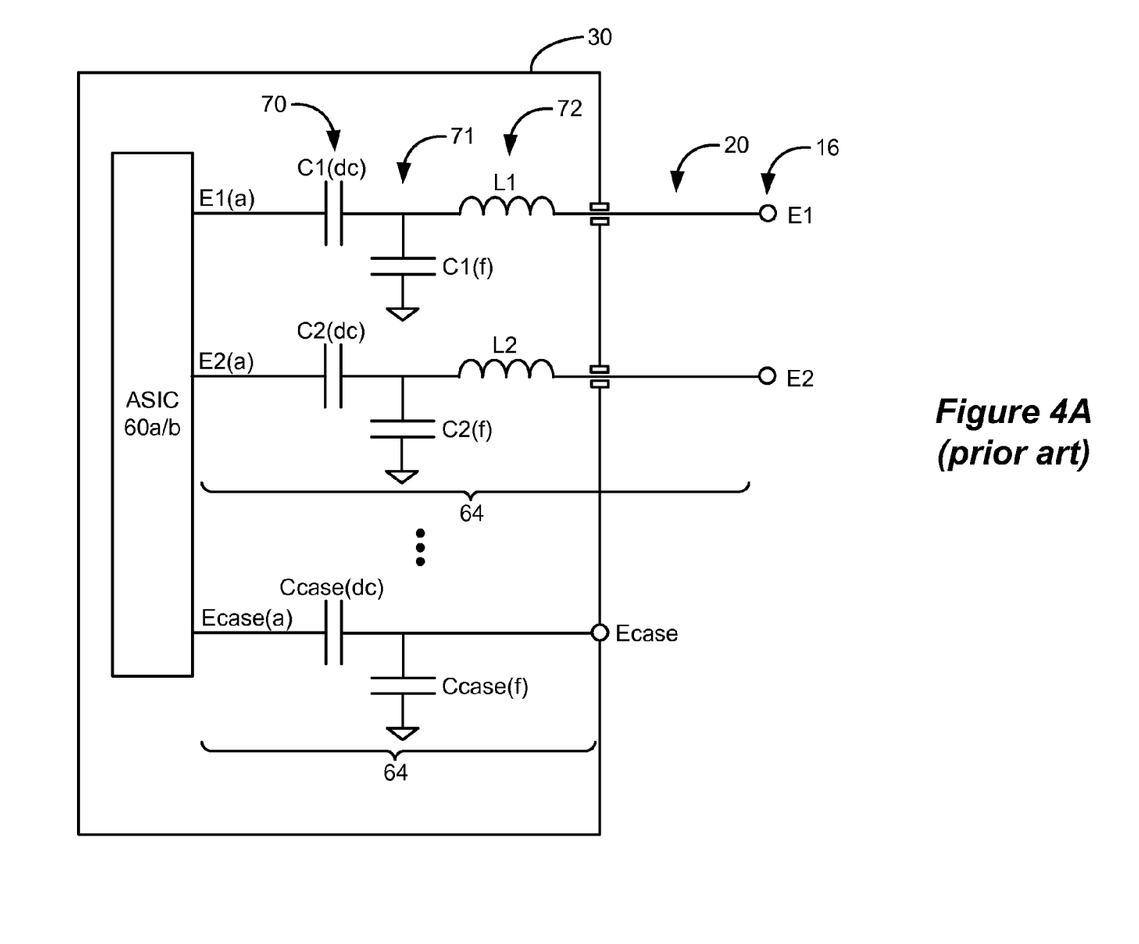
FIGS. 4A and 4B show the inclusion of filtering capacitors and filtering inductors in the electrode current paths, in accordance with the prior art.
Figure 4B:
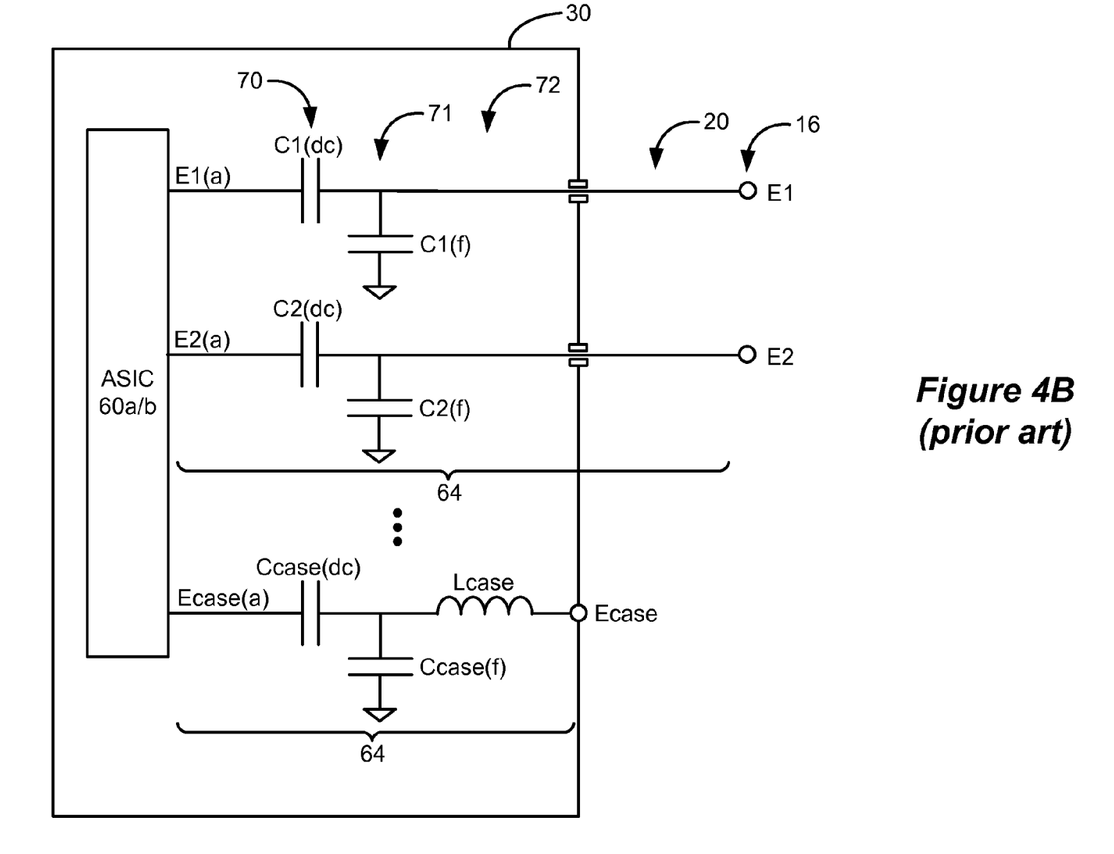

The problem of component size in an IPG is further exacerbated by newer advents that seek to add additional components to the IPG. For example, in U.S. Patent Application Publication 2014/0155970, which is incorporated herein by reference in its entirety, it is taught to use additional Electromagnetic Interference (EMI) filtering capacitors 71 (C(f)) in the electrode current paths 64, as shown in FIGS. 4A and 4B. These filtering capacitors 71 are coupled to the electrode current paths 64 in parallel between each of the electrode nodes Ei and a reference voltage (e.g., ground, such as the battery 36's negative terminal). As taught in the '970 Publication, filtering capacitors 71 are useful to shunt EMI coupled to the lead wires 20 to ground, such as the 64 MHz or 128 MHz frequencies typically present in a Magnetic Resonance Imaging (MRI) machine, and to hinder EMI from conducting to the conductive case 30. This reduces heating, and helps to protect the IPG circuitry from damage and from inadvertently stimulating the patient, thus making the IPG safer for use with patients requiring MRI procedures. Although not shown in FIGS. 4A and 4B, the '970 Publication teaches that the filtering capacitors 71 could also be coupled on the other side of the DC-blocking capacitors 70, i.e., in parallel between current distribution circuitry outputs Ei(a) and ground.

Also disclosed in the '970 Publication is the use of EMI filtering inductors 72 (Li), which like the DC-blocking capacitors 70 can placed in series in the lead electrode current paths 64, as shown in FIG. 4A, which filtering inductors Li can range from 0.5 to 3.0 microHenries. Alternatively, a single filtering inductor (Lcase) can be placed in the electrode current path of the case 30 having a value in the range of 50 to 200 nanoHenries, as shown in FIG. 4B.

The inventor recognizes that the '970 Publication discloses filtering capacitors 71 with values generally in the range of a few nanoFarads, which would be smaller in both capacitance and size when compared to the DC-blocking capacitors 70. For example, the inventor recognizes that filtering capacitors 71 could be implemented in an IPG 10 as 0805, 0603, or 0402 surface-mountable capacitors. Nonetheless, if filtering capacitors 71 are to be incorporated into IPG 10, space for such components must be found somewhere on the PCB 40 of the IPG 10, which space is already in short supply as noted earlier. If filtering inductors 72 are additionally incorporated into IPG 10, especially in each of the lead electrode current paths (Li; FIG. 4A), still more space in the IPG 10 would be needed.

A solution is therefore needed to accommodate these various electrode current path components, preferably in a manner that does not impact IPG flexibility in terms of the electrodes that can safely be chosen for patient therapy. Such solutions are provided in this disclosure.

DETAILED DESCRIPTION

Figure 5A:
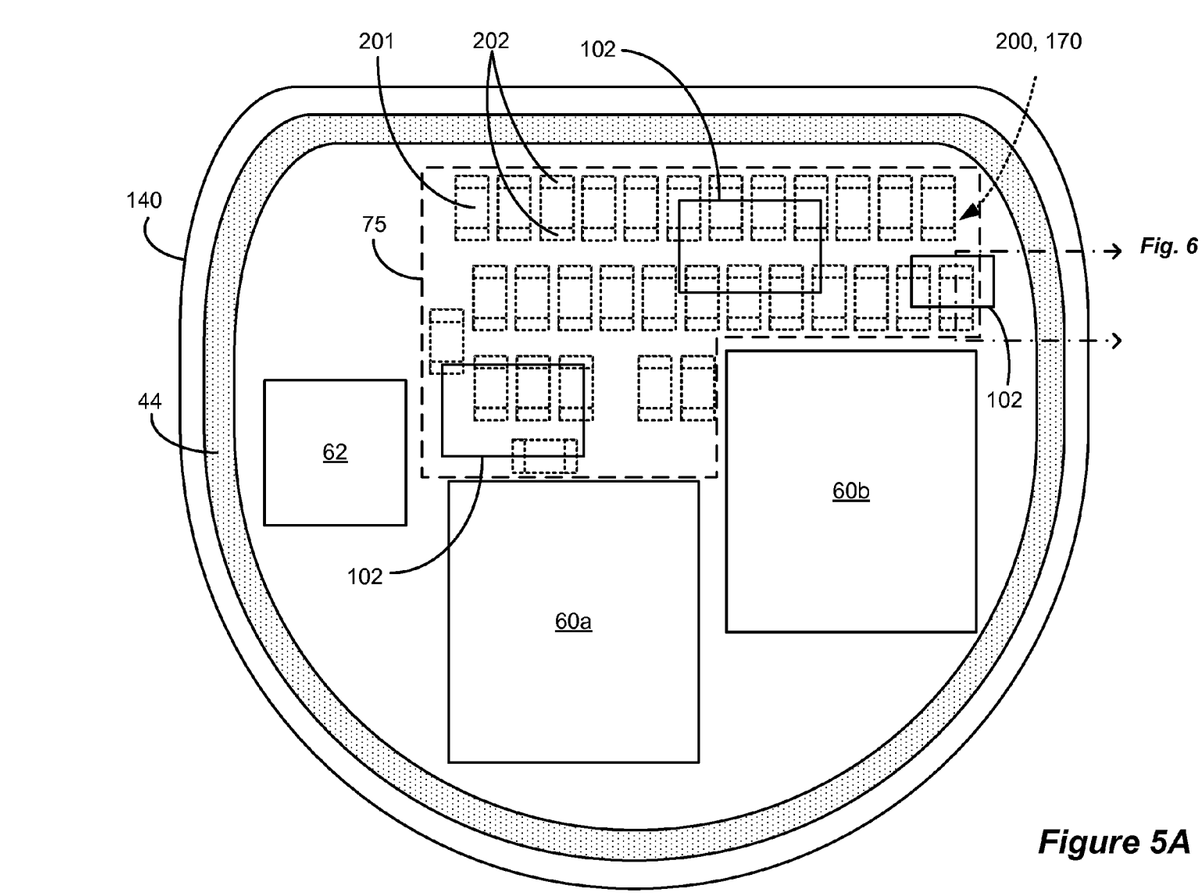
FIGS. 5A-5C show examples of an improved PCB for an IPG in which various components in the electrode current paths are embedded within the PCB, in accordance with examples of the invention.

FIG. 5A shows an improved printed circuit board (PCB) 140 for use with an IPG such as IPG 10. PCB 140 can be similar to PCB 40 illustrated earlier in FIG. 3, with its bottom surface also containing the ASICs 60a and 60b, the microcontroller 62, and the charging coil 44. However, one or more of the components in the electrode current paths 64 between the outputs Ei(a) of the current distribution circuitry (e.g., ASICs 60a/b) and the electrodes Ei and Ecase (16i, 30)—such as the DC-blocking capacitors 70, the filter capacitors 71, and/or the filtering inductors 72 (FIGS. 4A and 4B)—have now been embedded (200) within the internal layers of the PCB 140, and thus are shown in dotted lines.

As shown, the embedded components 200 comprise discrete components of the type traditionally surface mountable to a surface of the PCB 140, such as capacitor and inductor components having "XXYY"-type packages of the type described earlier, and thus have component bodies 201 and solderable terminals 202. However, this is not strictly necessary, and the particular construction of the embedded components 200 within PCB 140 can differ.

In the example shown in FIG. 5A, the embedded components 200 comprise the DC-blocking capacitors discussed earlier (70), now renumbered as 170 to reflect their embedded nature. Because the embedded DC-blocking capacitors 170 no longer occupy area 75 on the bottom surface of the PCB 140 (compare PCB 40; FIG. 3), other components 102 can be coupled to the PCB 140 within this area 75. Such other components 102 could comprise circuitry moved from elsewhere in the IPG 10, such as other circuitry 50a or 50b normally present on the top or bottom surfaces of the PCB (FIG. 1B), the microcontroller 62, either or both of ASICs 60a and 60b, etc. Area 75 can also accommodate additional DC-blocking capacitors, thus allowing the number of electrodes the IPG 10 can support to be doubled (e.g., from 32 to 64). Although not shown, such additional surface-mounted DC-blocking capacitors (70) in area 75 could directly overlie the embedded DC-blocking capacitors 170.

Area 75 can also accommodate additional circuitry not otherwise used in traditional IPGs but desirable to add given the additional room provided by area 75, such as the filtering capacitors 71 or filtering inductors 72 of FIGS. 4A and 4B in one example, thus promoting the addition or extension of IPG functionality. Although FIG. 5A shows that all DC-blocking capacitors 170 have been embedded in the PCB 140, this is not strictly required. For example, half (e.g., sixteen) may be embedded (170), with the other half being traditionally surface mounted (70; FIG. 3).

As shown in FIG. 5A, the DC-blocking capacitors 170 have been embedded in the PCB 140 below their previously-illustrated positions on the bottom side of the PCB 40 (FIG. 3). However, such positioning is not strictly necessary, and the DC-blocking capacitors 170 or other embedded components 200 discussed subsequently can be embedded anywhere in PCB 140, possibly in different non-adjacent areas. Area 75 may thus define the surface area of the PCB 140 above and/or below the embedded components 200 wherever they are located, and without reference to previous positions.

Assuming area 75 is not used to add additional circuitry to the IPG 10, moving pre-existing IPG components into area 75 allows the PCB 140 to be made smaller compared to PCB 40 (FIG. 3), which allows the IPG 10 to be made smaller, promoting patient comfort and easing implantation concerns. Notwithstanding this reduction in size, an embedded DC-blocking capacitor 170 is still provided in series in the electrode current path 64 for each electrode 16 supported by the IPG 10, which as noted earlier prevents DC current injection into the patient and promotes patient safety. Because a DC-blocking capacitor 170 is provided with each selectable electrode 16, the electrodes 16 can be freely selected as anodes or cathodes without concern of DC current injection from a chosen electrode current path 64, and without complicating the design of the current distribution circuitry in the IPG 10, which can otherwise remain as illustrated in FIGS. 2A and 2B. As noted earlier, a one-to-one correspondence between IPG-supported electrodes and DC-blocking capacitors is not suggested by prior art space-saving techniques, which instead reduce the number of DC-blocking capacitors relative to the number of IPG electrodes.

Figure 5B:
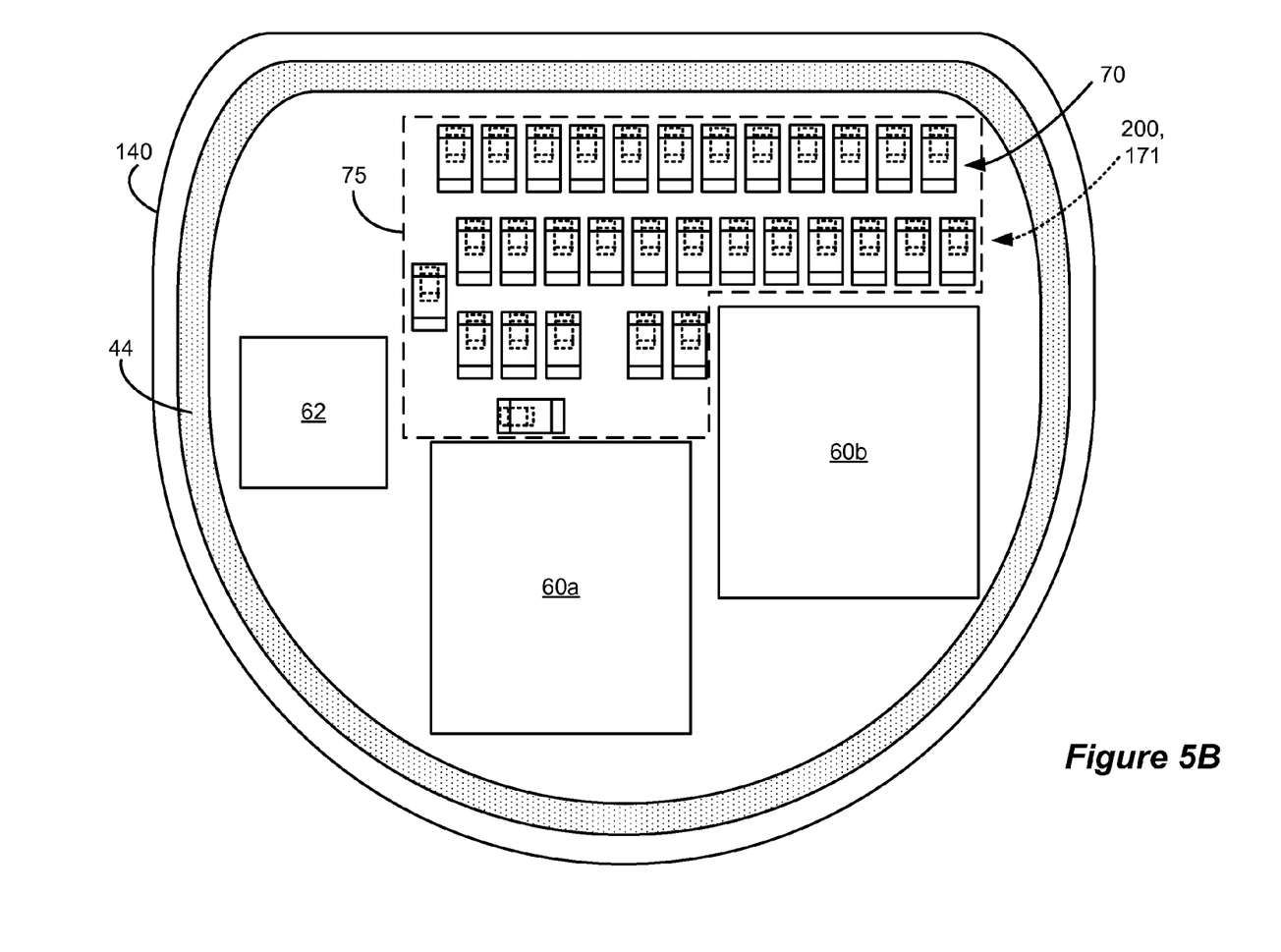
Figure 5C:
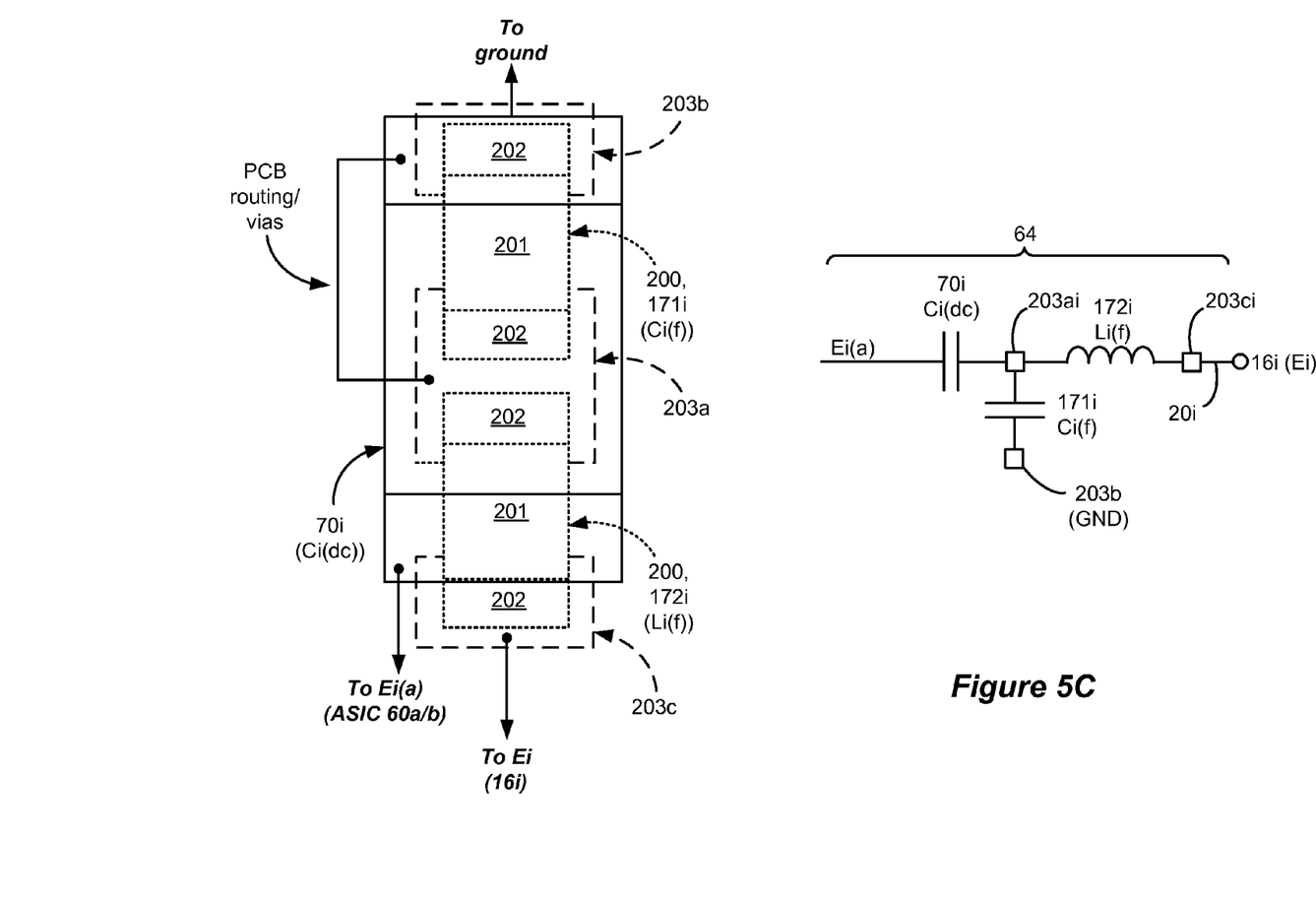

FIGS. 5B and 5C show other alternatives for embedding different components 200 in the electrode current paths 64 within the PCB 140. In the example shown in FIG. 5B, the embedded components 200 comprise the EMI filtering capacitors of the '970 Publication discussed earlier (71; FIGS. 4A and 4B), renumbered as 171 to reflect their embedded nature. The DC-blocking capacitors 70 are surface mounted to the PCB 140 and otherwise occupy the same position in area 75 illustrated earlier in FIG. 3. Note that in this example, the IPG 10 is provided with additional MRI filtering capability as taught in the previously-incorporated '970 Publication (FIGS. 4A and 4B), but without increasing the size of the PCB 140 relative to its earlier design 40 (FIG. 3), and without the need to significantly change the layout and position of other devices on the PCB. This is especially preferred for convenience and so as not to upset legacy PCB 40 designs.

The example of FIG. 5B is also preferred because, as realized by the inventor, the capacitance values and sizes of the filtering capacitors 171 are smaller than the DC-blocking capacitors 70. For example, while the DC-blocking capacitors may comprise 1206 or 0805 capacitors, the filtering capacitors 171 may comprise smaller 0805, 0603, or 0402 capacitors, which are easier to embed given their smaller size. As shown in FIG. 5B, the embedded filtering capacitors 171 are generally located below each of the DC-blocking capacitors 70 with which they are associated, which eases routing in the PCB 140 to couple the DC-blocking capacitors 70 and the filtering capacitors 171 to their electrode current paths 64. However, this is not strictly necessary, and the particular placement of the embedded filtering capacitors 171 relative to the surface-mounted DC-blocking capacitors 70 can vary. Not all of the filtering capacitors 171 need be embedded in the PCB 140; some can be traditionally surface mounted. Routing in PCB 140 with embedded components 200 is discussed subsequently.

FIG. 5C takes FIG. 5B further by additionally including the filtering inductors in each of the lead electrode current paths 64 (72; FIG. 4A) as embedded components 200 (renumbered as 172) along with the embedded filtering capacitors 171. As shown, each embedded filtering capacitor 171*i* and embedded filtering inductor 172*i* are coupled within the PCB 140 to internal PCB contacts 203 to effectuate the electrode current path circuitry 64, which in this example includes a surface-mounted DC-blocking capacitor 70*i*. Internal PCB contacts 203 occur at a conductive layer (Cu*i*) in the PCB 140, as will be discussed shortly. Connection to other circuit nodes can be effectuated by routing in the PCB 140, which may include the use of conductive vias 106, 108 (FIGS. 7A, 7B) between different conductive layers, as illustrated subsequently and as one skilled will appreciate.

In the example in FIG. 5C, the embedded filtering capacitors 171 and embedded filtering inductors 172 are one-quarter of the area (i.e., half the linear size) of the DC-blocking capacitors 70—for example, "1206" DC-blocking capacitors 70 and "0603" embedded filtering capacitors 171 and filtering inductors 172. "0603" surface mount inductors with inductance values suitable for EMI filtering are sold by NIC Components Corporation of Melville, N.Y. See http://www.niccomp.Com/catalog/nfp.pdf. Thus, the embedded filtering capacitors 171 and filtering inductors 172 can be located underneath the surface-mounted DC-blocking capacitors 70 with which they are associated, without need to re-position such DC-blocking capacitors 70 from surface mounted positions in area 75 in legacy PCBs 40 (FIG. 3). However, such legacy positioning is also not strictly necessary. Nor is it necessary that the size of the embedded filtering capacitors 172 and filtering inductors 172 be equal, or that such devices appear under their DC-blocking surface-mounted capacitors 70. Other layout schemes are plausible to generally locate the embedded filtering capacitors 171 and filtering inductors 172 underneath the DC-blocking capacitors 70 with which they are associated, or there may be no association in such positions. Not all of the filtering inductors 172 need be embedded in the PCB 140; some can be traditionally surface mounted.

Despite the specific non-limiting examples shown in FIGS. 5A-5C, it should be noted that other combinations of the components in the electrode current paths 64—the DC-blocking capacitors (Ci(dc)), the filtering capacitors (Ci(f)), and/or the filtering inductors (Li(f))—can be embedded 200 or surface mounted to the PCB 140. For example, the DC-blocking capacitors could be embedded, while the filtering capacitors are surface mounted. The filtering inductors could instead be surface mounted, even if the filtering capacitors are embedded. Less than all of any of these components 70, 71, and 72 (FIGS. 4A and 4B) could be embedded, or they all could be. In short, any combination or number of these components could be embedded in the PCB 140, leaving the remainder (if any) to be surface mounted at area 75 or elsewhere on the PCB 140.

Technologies for embedding components 200 within a PCB are known, and some of these technologies are subsequently discussed with reference to FIGS. 7A and 7B. Before turning to those figures, a generic illustration of an embedded component 200*i* in PCB 140 is shown in cross section in FIG. 6, which could comprise an embedded DC-blocking capacitor 170*i*, an embedded filtering capacitor 171*i*, an embedded filtering inductor 172*i*, or another IPG component, whether in an electrode current path 64 or not. As seen, the embedded component 200*i* is wholly recessed below the top 140*a* and bottom 140*b* surfaces of the PCB 140 where components (e.g., 102) are traditionally coupled.

Figure 6:
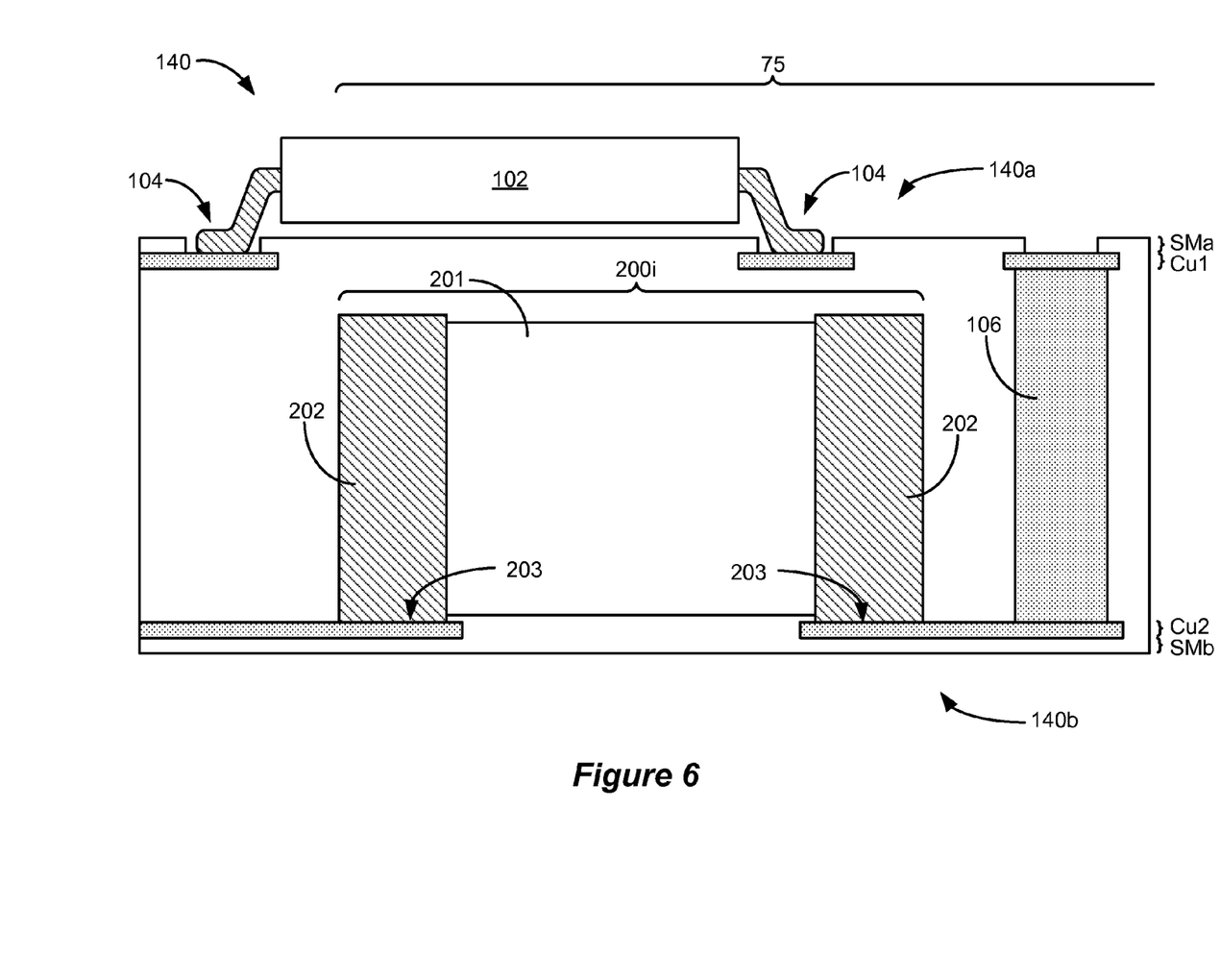
FIG. 6 shows a generalized cross section of an embedded component in the improved PCB for an IPG, in accordance with an example of the invention.

As shown, the component terminals 202 are connected at internal PCB contacts 203 (FIG. 5C) to a patterned copper conductive layer Cu2 proximate to the bottom surface 140*b* of the PCB 140. Other components (e.g., 102) at the top surface 140*a* of the PCB 140 are coupled to a conductive layer Cu1 at external PCB contacts 104 formed in a top solder mask layer SMa. (As shown in subsequent examples, the PCB 140 may contain more than two conductive layers). Although not shown for convenience, other components 102 could likewise be connected to conductive layer Cu2 at the bottom surface 140*b* of the PCB 140 at external PCB contacts 104 formed in bottom solder mask layer SMb. Thus, such other components 102 may appear within or without area 75 above or below the embedded components 200. Components 102 need not merely be surface mountable to the PCB 140, and instead the PCB 140 may employ through-hole technology to receive leads from such components. A conductive via 106 is shown connecting conductive layers Cu1 and Cu2 to assist with PCB routing.

Figure 7A:
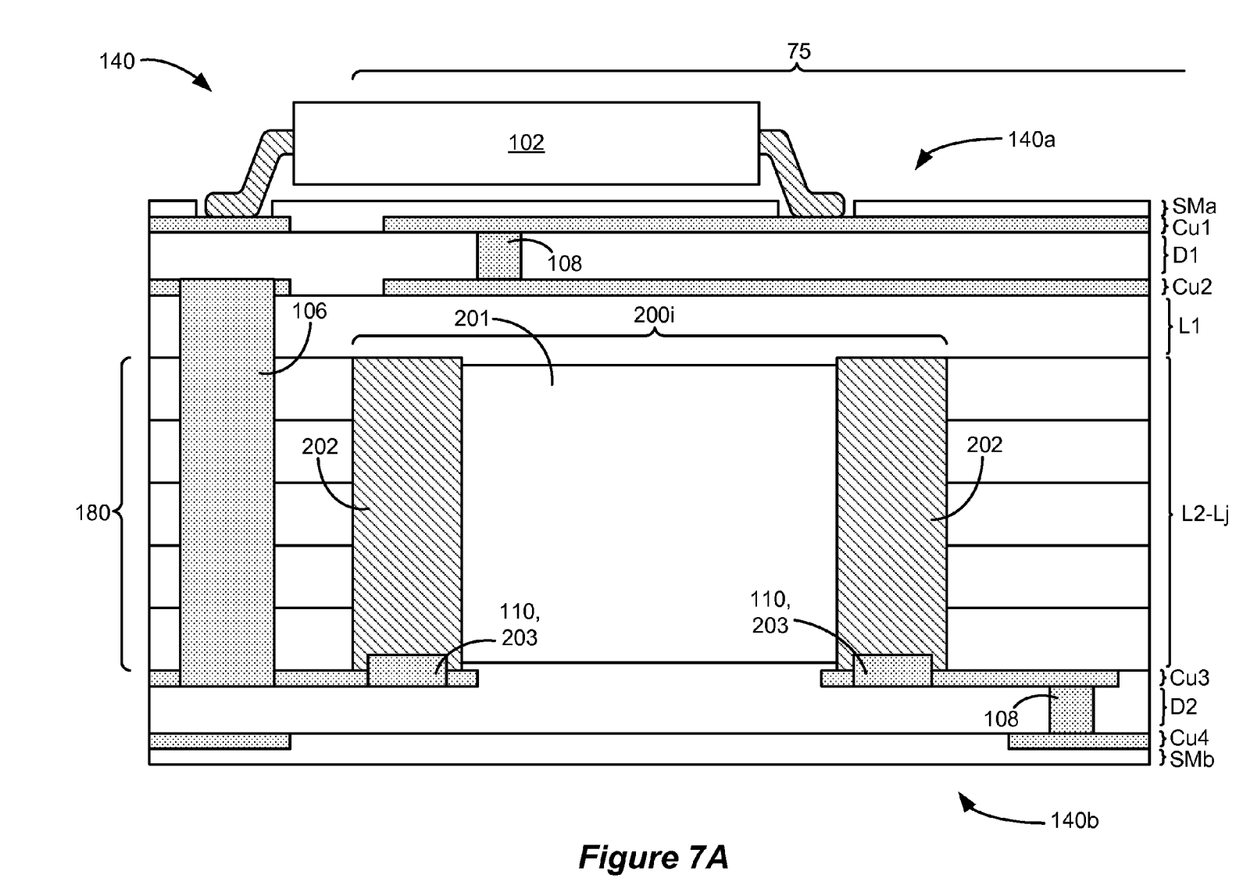
FIGS. 7A and 7B show different fabrication methods by which components can be embedded in a PCB for an IPG, in accordance with examples of the invention.
Figure 7B:
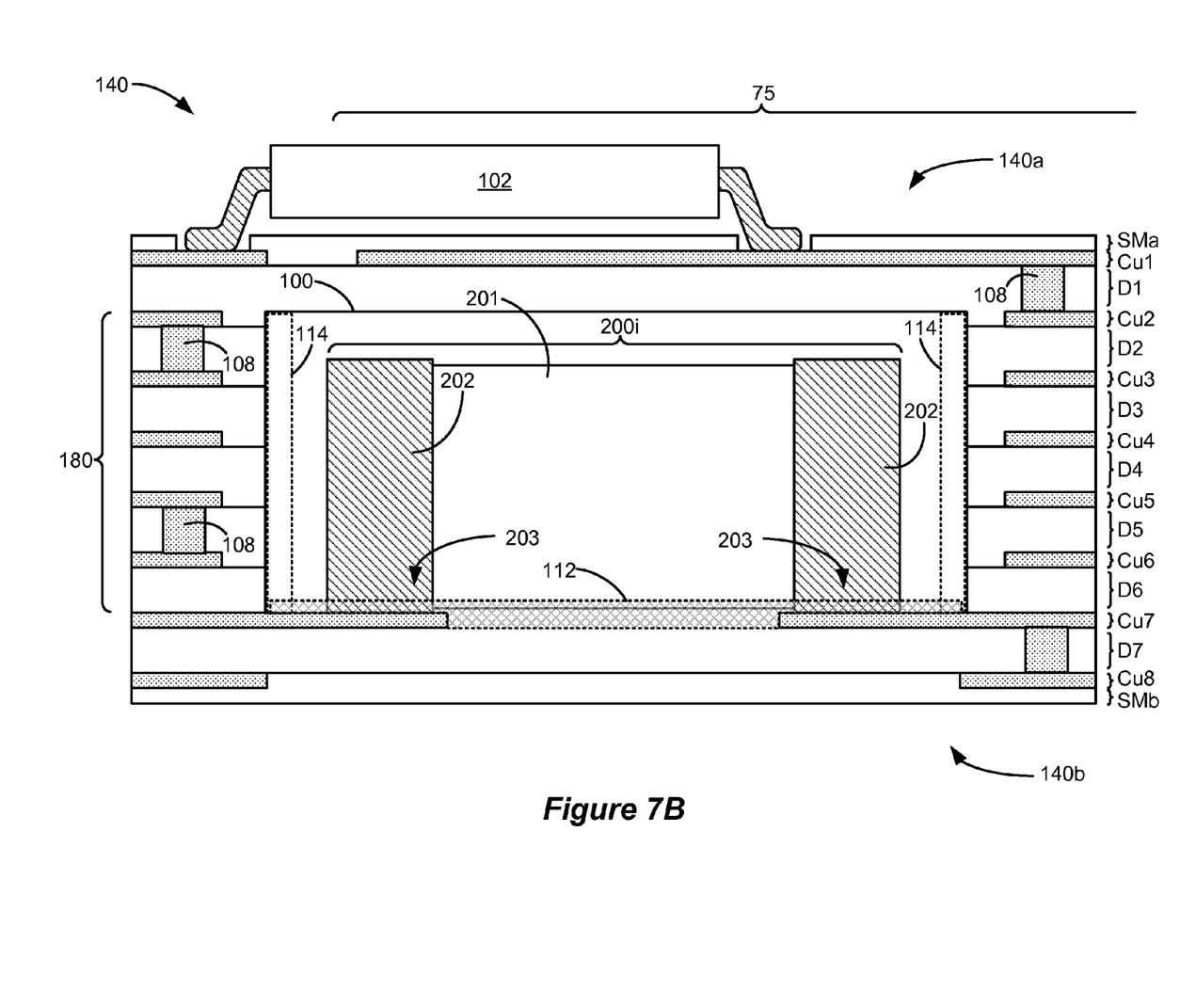

FIGS. 7A and 7B illustrate further details regarding PCB 140 formation and how components 200 can be embedded in the PCB 140. These illustrated fabrication examples differ in certain respects, and in particular regarding whether conductive layers (Cu*i*) can occupy the thickness 180 in the PCB 140 occupied by the embedded components 200. Regardless, conductive layers can occupy PCB layers above or below the embedded components 200 within area 75, thus permitting the addition of circuitry at those surfaces.

In FIG. 7A, no conductive layers are present in the PCB 140 at PCB levels occupied by the embedded component thickness 180. The PCB 140 fabrication technique of FIG. 7A is generally illustrated in "Embedded Device Packaging Ramping Up Next Generation SiP," JISSO European Council Seminar, Nurnberg, Del., pg. 16 (May 2011); and H. Haidinger, "Cost Driver for PCB with Advanced Technologies," pg. 18-19, AT&S Technology Forum (2013), and therefore are only briefly described.

The process starts using a substrate (not shown) upon which a copper sheet (Cu3 in the depicted example) is placed. An adhesive (not shown) is printed on layer Cu3 in the positions of the components 200, and the components 200 are adhered thereto. Dielectric laminate layers (L2-Lj) pre-formed to contain holes at the locations of the adhered components 200 are slipped over these components. A final laminate layer L1 not containing holes is then placed on top. The number and thickness of the laminate layers will depend on the thickness of the embedded components 200 as well as other design rules for the PCB 140.

Next, another substrate (not shown) upon which another copper sheet is formed (Cu2 in the depicted example) is inverted and placed over laminate L1. The resulting stack is then pressed at high temperature to cause the laminate layers to flow and surround the components 200, and to otherwise to rigidly adhere the various layers in the stack together. At this point, the stack is bounded at its top and bottom by the not-yet patterned conductive layers Cu2 and Cu3.

Next, holes are mechanically drilled through the structure in the future locations of the vias 106. A UV laser is then used to drill through the bottom Cu3 layer and through the not-shown adhesive to expose the component terminals 202. After de-smearing the resulting holes with a $CO_2$ laser, the resulting structure is then masked and metallized to form the vias 106 and to couple 110 the component terminals 202 to conductive layer Cu3, thus forming the internal PCB contacts 203 mentioned earlier (FIG. 5C). (Although not shown, resulting vias 106 may be hollow). Any remaining adhesive in the resulting structure may degrade during PCB fabrication and does not affect PCB performance.

Thereafter, the remaining structure can be processed using conventional PCB formation techniques to build up further conductive layers and to complete PCB 140 fabrication. For example, the conductive layers Cu2 and Cu3 can be patterned as desired, with additional dielectric layers D1 and D2 placed on them containing vias 108 as necessary, etc. Thus, PCB 140 can contain as many conductive layers as is necessary or practical outside of the thickness 180, and above and below the embedded component 200 in area 75. One skilled will understand that the composition of the various dielectric layers (Li and Di) may vary, but would generally comprise known PCB materials, such as FR4, prepreg, etc. Laminate layers Li may be designed to flow so as to encapsulate the components 200, whereas other traditional dielectric layers Di used outside of thickness 180 may comprise low- or no-flow materials.

FIG. 7B employs a technique in which one or more cavities 100 are formed in the PCB 140, as described in M. Leitgeb, "2.5D Technology Platform," pg. 4, 22-29, AT&S (Feb. 28, 2013); and M. Leitgeb, "Modulare Integrationskonzepte: Miniaturisierung & Funktionale Integration Darstellung der Vorteile & der Umgesetzten Produktideen," pg. 16-17, AT&S Technologieforum (Oct. 9, 2013), and therefore are only briefly described. In FIG. 7B, conductive layers (e.g., Cu2-Cu6) can be present in the PCB 140 at PCB levels occupied by the component thickness 180, as well as inside or outside of area 75. As such, PCB routing is generally eased when compared to the PCB fabrication process of FIG. 7A, and as such FIG. 7B may result in a smaller PCB 140.

PCB fabrication can start conventionally with a subassembly in which a conductive layer that will comprise the bottom of the cavity/ies 100 (layer Cu7 in the depicted example) is formed and patterned over underlying layers. (Underlying dielectric layer D7 and conductive layer Cu8 are shown, but this is merely one example and other dielectric/conductive layers could be present in the subassembly). A release layer 112 is patterned on Cu7 generally corresponding with the desired position of the cavity/ies 100.

Additional dielectric and patterned conductive layers (e.g., D2-D6; Cu2-Cu6) are stacked conventionally to the thickness of the desired cavity/ies 100. Note that these patterned conductive layers are preferably absent in the area corresponding to the future cavity/ies 100, and can also be absent from the entirety of area 75 where the embedded components 200 will generally be located.

A laser is used to cut 114 through the top surface (e.g., at Cu2) around a periphery of the desired cavity/ies 100 down to the release layer 112. Upon exposure to a solvent for example, the release layer 112 will dissolve, thus allowing layers in the cavity/ies 100 (D2-D6) to be removed as a cap or plug. At this point, the embedded components 200 can be positioned in the cavity/ies 100 and coupled (e.g., by ultrasonic bonding) to the already-patterned underlying conductive layer at the bottom of the cavity/ies (i.e., Cu7), thus establishing internal PCB contacts 203 (FIG. 5C). Note that the components 200 could each be embedded in the PCB 140 in their own individual cavities 100, or they could be embedded in one or more cavities. Thereafter, a dielectric layer (e.g., D1) is adhered to the top surface to enclose the cavity/ies 100 and the embedded components 200. If desired the cavity/ies 100 can be filled with a dielectric such as an epoxy before being covered by subsequent layers. The remaining structure can be processed using conventional PCB formation techniques to build up further conductive layers on the top and bottom surfaces to complete PCB 140 fabrication.

Other techniques may also be used for embedding components in the PCB 140, as referenced in the attached Information Disclosure Statement reference listing.

The inventor realizes that an embedded component in a PCB need not comprise a packaged component, such as the discrete capacitors or inductors as illustrated to this point. For example, an embedded PCB capacitor component may come from use of particular dielectric layers in the PCB itself. In this regard, PCB suppliers offer materials for this purpose, such as ceramic-filled epoxies sandwiched between layers of copper foil. See, e.g., "3M Embedded Capacitance Material (ECM)" 3M Company (2013). At current, the capacitance of such materials (e.g., 3.1 $nF/cm^2$) may be too small to form embedded DC-blocking capacitors 170 or embedded filtering capacitors 171 in some IPG applications. However, as this technology progresses, such PCB-embedded materials will become suitable for a wider range of IPG applications. Embedded PCB inductor components useful as the embedded filtering inductors 172 may come from forming turns in the various conductive layers in the PCB 140, with turns in the layers connected by vias 108. Indeed, one or more of the telemetry 42 or charging coils 44 could also be embedded in the PCB 140 in this fashion.

While embedding of components in the electrode current paths in a PCB of an IPG is considered uniquely beneficial given the large number and area of these components, the inventor recognizes that still other components typically mountable to a surface of an IPG's PCB could also be embedded, whether in the electrode current paths or not, such as resistors, various integrated circuits (e.g., the microcontroller 62, one or both of the ASICs 60a and 60b, etc.), accelerometers, Reed magnetic field sensors, temperature sensors, capacitors and inductors used for other purposes, etc. As such, embedded components 200 need not comprise simple two-terminal, unpowered, passive, linear devices such as capacitors, inductors, and resistors, but could also include multi-terminal, powered, active, or non-linear devices or circuitry.

A "component" embedded in a circuit board as used herein should be understood as a structure intentionally included in the PCB to affect the operation of the circuitry, as thus excludes traditional routing structures normally embedded in PCBs such as conductive traces formed in the conductive layers (Cui), the vias (106, 108), etc.

To this point, the case electrode 30 (Ecase) has been treated more or less synonymously with the other lead electrodes 16 (Ei), in that it may be selectable as an anode or cathode, can contain the same components 70-72 or 170-172 in its electrode current path, etc. However, the case electrode 30 may in some IPG architectures be governed by different considerations. For example, it may merely couple to a passive reference voltage as opposed to being driven with a current; it may or may not have a DC-blocking capacitor; it may or may not contain filtering components, or may contain such components but with different values, etc. Thus, while the case electrode may comprise one of the plurality of electrodes Ei as recited in the claims below, the case electrode may also be excluded from that set.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable stimulator device, comprising:
    a plurality of electrodes configured to contact tissue of a patient;
    a circuit board having a top surface and a bottom surface;
    current distribution circuitry integrated on an integrated circuit mounted to the top surface of the circuit board, wherein the current distribution circuitry comprises source circuitry configured to generate a current at one or more of a plurality of selectable outputs, each output coupled to one of the electrodes via an electrode current path; and
    a plurality of DC-blocking capacitors, each DC-blocking capacitor coupled in series in one of the electrode current paths,
    wherein the DC-blocking capacitors are embedded below the top surface and above the bottom surface of the circuit board.

2. The device of claim 1, wherein the DC-blocking capacitors are embedded above or below at least one area on a surface of the circuit board, and wherein the circuit board comprises other circuitry coupled to the surface within the at least one area.

3. The device of claim 1, wherein the DC-blocking capacitors are embedded in at least one cavity within the circuit board.

4. The device of claim 1, wherein the DC-blocking capacitors occupy a thickness within the circuit board, and wherein the circuit board does not contain conductive layers within the thickness.

5. The device of claim 1, wherein the DC-blocking capacitors occupy a thickness within the circuit board, and wherein the circuit board contains at least one conductive layer within the thickness.

6. The device of claim 1, wherein each DC-blocking capacitor comprises a packaged component.

7. The device of claim 1, further comprising a plurality of second components, each second component coupled to one of the electrode current paths.

8. The device of claim 7, wherein the second components are coupled to a surface of the circuit board.

9. The device of claim 8, wherein the DC-blocking capacitors are embedded above or below at least one area on the surface of the circuit board, and wherein the second components are coupled to the surface within the at least one area.

10. The device of claim 8, wherein the second components comprise filtering capacitors.

11. The device of claim 10, wherein the filtering capacitors couple interference on the electrode current paths to a reference potential.

12. The device of claim 1, further comprising a case operable as a case electrode, wherein the case electrode comprises one of the plurality of electrodes.

13. The device of claim 1, further comprising a case operable as a case electrode, wherein the case electrode does not comprise one of the plurality of electrodes.

14. An implantable stimulator device, comprising:
    a plurality of electrodes configured to contact tissue of a patient;
    a circuit board having a top surface and a bottom surface;
    current distribution circuitry integrated on an integrated circuit mounted to the top surface of the circuit board, wherein the current distribution circuitry comprises source circuitry configured to generate a current at one or more of a plurality of selectable outputs, each output coupled to one of the electrodes via an electrode current path;
    a plurality of DC-blocking capacitors, each DC-blocking capacitor coupled in series in one of the electrode current paths; and
    a plurality of filtering capacitors, each filtering capacitor coupled in parallel between one of the electrode current paths and a reference potential,
    wherein the DC-blocking capacitors are embedded below the top surface and above the bottom surface of the circuit board.

15. The device of claim 14, wherein the embedded DC-blocking capacitors are embedded above or below at least one area on a surface of the circuit board, and wherein the circuit board comprises other circuitry coupled to the surface within the at least one area.

16. The device of claim 14, wherein the embedded DC-blocking capacitors are embedded in at least one cavity within the circuit board.

17. The device of claim 14, wherein the embedded DC-blocking capacitors occupy a thickness within the circuit board, and wherein the circuit board does not contain conductive layers within the thickness.

18. The device of claim 14, wherein the embedded DC-blocking capacitors occupy a thickness within the circuit board, and wherein the circuit board contains at least one conductive layer within the thickness.

19. The device of claim 14, wherein each embedded DC-blocking capacitor comprises a packaged component.

20. The device of claim 14, further comprising a conductive case, wherein the reference potential does not comprise a voltage of the conductive case.

21. The device of claim 14, wherein the filtering capacitors are also embedded in the circuit board.

22. The device of claim 14, wherein the filtering capacitors are coupled to a surface of the circuit board over the embedded DC-blocking capacitors.

23. The device of claim 14, further comprising a plurality of inductors, each inductor coupled in series in one of the electrode current paths.

* * * * *